United States Patent [19]
Singh et al.

[11] Patent Number: 4,784,648
[45] Date of Patent: * Nov. 15, 1988

[54] INFILTRATION INDICATOR AND ALARM

[75] Inventors: Param I. Singh, Lexington; Saul Stricker, Marblehead, both of Mass.

[73] Assignee: Applied Biomedical Corporation, Danvers, Mass.

[*] Notice: The portion of the term of this patent subsequent to Dec. 2, 2003 has been disclaimed.

[21] Appl. No.: 907,413

[22] Filed: Sep. 15, 1986

[51] Int. Cl.⁴ .................................................. A61M 5/00
[52] U.S. Cl. ..................................... 604/141; 604/246; 138/44
[58] Field of Search ............... 604/118, 131, 140–148, 604/246; 138/40, 44, 45; 222/95, 96, 105

[56] References Cited

U.S. PATENT DOCUMENTS

| | | | |
|---|---|---|---|
| 2,319,498 | 5/1943 | Gerard | 138/45 X |
| 3,298,367 | 1/1967 | Bergman | 604/246 |
| 3,469,578 | 9/1969 | Bierman | 604/246 X |
| 3,517,700 | 6/1970 | Williams et al. | 138/44 |
| 3,640,277 | 2/1972 | Adelberg | 604/141 |
| 3,831,588 | 8/1974 | Rinder | 604/118 X |
| 3,850,348 | 11/1974 | Bessot et al. | 604/141 X |
| 4,626,243 | 12/1986 | Singh et al. | 604/141 |

Primary Examiner—Stephen C. Pellegrino
Attorney, Agent, or Firm—Gurdon R. Abell

[57] ABSTRACT

In an infusion system, a source of pressurized liquid infusate is connected to the upstream end of a small-bore flow restrictor and drives a flow of infusate therethrough; the downstream end of the flow restrictor is connected to the patient. The infusate at the upstream end is in communication with an annulus inflatable by infusate pressure of at least 200 to 500 Torr; the infusate at the downstream end is in communication with another annulus inflatable by infusate pressure of only 35 to 110 Torr, as occurs during infiltration. Inflation of an annulus provides a visible indication and can provide electrical contact for an alarm.

5 Claims, 1 Drawing Sheet

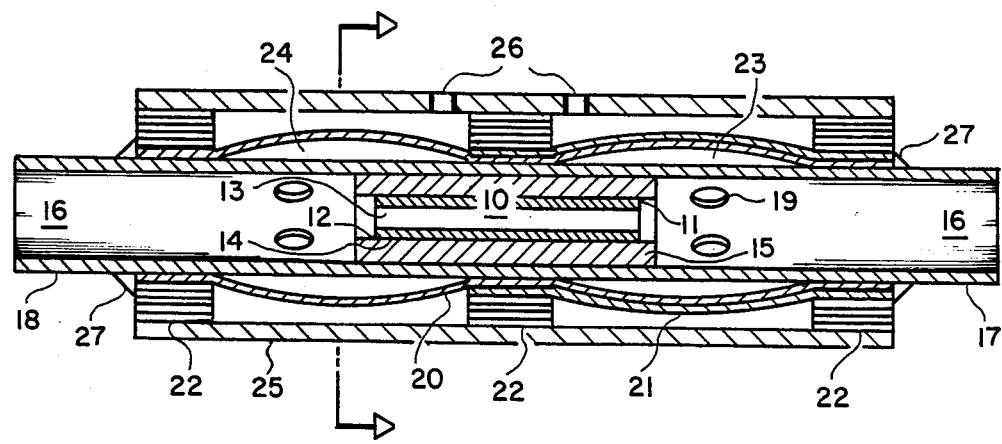
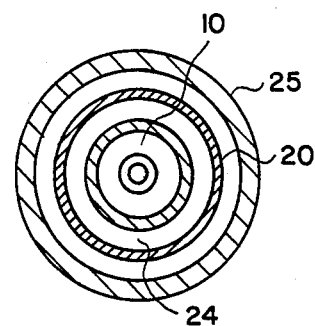
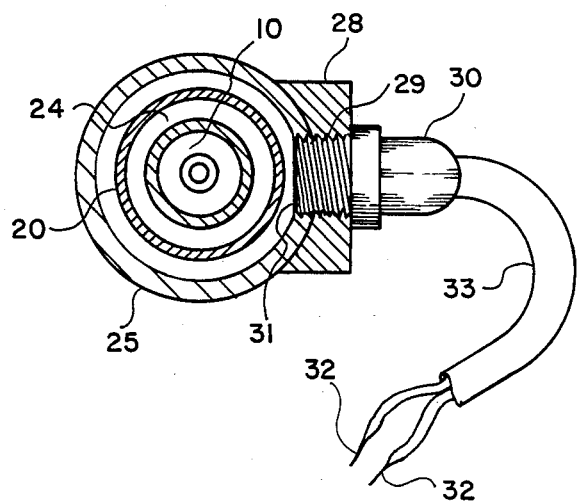

INFILTRATION INDICATOR AND ALARM

CROSS-REFERENCE TO RELATED APPLICATION

This application is related to application Ser. No. 06/749,470 of Param I. Singh and David C. deSieyes, filed June 21 1985, now U.S. Pat. No. 4,626,243, and assigned to the same assignee as this application. The disclosure of that application and patent is incorporated herein by reference, as if set out at length.

FIELD OF THE INVENTION

This invention relates generally to apparatus for infusing medically necessary liquids into a living patient at a desired rate determined, at least in part, by hydraulic resistance of a flow restrictor, and this invention relates more particularly to such restrictors in which the hydraulic resistance is provided by a small-bore flow passage such as a length of capillary tubing.

PRIOR ART PROBLEM

A continuing problem, particularly in intravenous infusions, is that of "infiltration". This term denotes deposition of infusate into tissues surrounding the vein due to misplacement or displacement of the infusion needle. Such deposition can cause pain in most cases and destruction of tissue in some cases, and is to be avoided, or at least detected quickly enough to permit prompt repositioning of the needle.

SUMMARY OF THE INVENTION

It is accordingly the principal object of this invention to provide an infiltration indicator and alarm which will sense and display the onset or existence of the infiltration condition. According to this invention, advantage is taken of the fact that the liquid pressure in the infusion needle, when infiltration is occurring, is typically in the range of 35–110 Torr, considerably greater than ordinary intravenous pressure but also considerably less than the 200–500 Torr driving pressure in a high-driving-pressure infusion system such as that disclosed in the related application identified hereinabove. In that application, there was disclosed a restrictor incorporating flow and pressure indicator means comprising elastomeric tubing annuli, upstream and downstream of the small-bore passage, inflatable by high driving pressure to indicate presence of that high pressure at those locations. According to the present invention, at least the annulus at the downstream end of such a restrictor, nearest the patient, is made sufficiently easily distensible to be inflatable by pressures in the range of 35–110 Torr, thus, responding to the pressure condition accompanying infiltration. Further according to this invention, inflation of an annulus may close electrical contacts, thus providing alarm means for sensing the existence of the infiltration condition. Other objects of this invention, as well as the means for attaining them, are set forth in the accompanying Specification and Drawings, wherein:

BRIEF DESCRIPTION OF THE DRAWINGS

FIG. 1 is a longitudinal cross-section of a flow restrictor which incorporates means for indicating the presence of elevated infusion pressure signifying the existence of infiltration;

FIG. 2 is an axial cross-section of the flow restrictor shown in FIG. 1, in the direction denoted by 2—2 in that Figure; and FIG. 3 is a similar view, largely in axial cross-section, of a flow restrictor similar to that shown in FIG. 1, having further means for providing an alarm signal signifying the existence of infiltration.

DESCRIPTION OF THE INVENTION

Reference is made to FIGS. 1 and 2, which are respectively a longitudinal cross-section and an axial cross-section of a flow restrictor according to this invention. The flow restrictor comprises a cylindrical flow resistance element 10 having an upstream end 11 and a downstream end 12 with flow resistance provided by a small-bore flow passage 13; in the illustrated embodiment; flow resistance element 10 comprises a length 14 of capillary tubing snugly held in slightly longer length 15 of elastomeric tubing. This assembly is snugly mounted within a long rigid tube or duct 16, having upstream and downstream ends 17 and 18, and provided with holes 19 just outside the upstream and downstream ends 11 and 12 of flow resistance element 10.

Surrounding duct 16 is a long closely-fitting thin-wall elastomeric tube 2 which extends beyond holes 19 in both the upstream and downstream directions; the upstream half of tube 20 is in turn surrounded by an additional closely-fitting elastomeric tube 21. These tubes are joined to duct 16 by tight wrappings 22 to form an upstream inflatable annulus 23 and a downstream inflatable annulus 24 which are both in fluid communication with the interior of duct 16 through holes 19. This assembly is then placed within a transparent cylindrical spaced-apart jacket 25 which is provided with small vent holes 26. The joints between duct 16 and tubes 20 and 21 may be reinforced with some added adhesive 27. Upstream and downstream ends 17 and 18 of duct 16 may be joined to associated tubing of the infusion system either by wrappings such as those shown at 22 or in any other conventional way, compatible with elevated drive pressures, such as "Luer Lock" fittings.

The thickness and elastic modulus of tube 20 defining downstream annulus 24 are sufficiently small to permit inflation of annulus 24 to bear upon the inner surface of transparent jacket 25 when the pressure of the infusant at the downstream end 18 of duct 16 is only 35 to 110 Torr. The thickness and elastic modulus of tube 21, together with those of tube 20, both defining upstream annulus 23, permit corresponding inflation of that annulus at infusant drive pressure in the range of 200 to 500 Torr.

The inner surface of transparent jacket 25 is optically rough or frosted, so that it appears white unless touched by the outer surface of an inflatable annulus, whereupon optical internal reflection at the inner surface of jacket 25 is largely frustrated and the surface takes on essentially the spectral absorptance characteristics of the outer surface of the annulus. To exploit this fact, the outer surface of tube 21 at upstream annulus 23 is colored green, and the outer surface of tube 20 at downstream annulus 24 is colored red. Therefore, the appearance of a green band of color signifies the presence of adequate driving pressure, but a red band of color signifies the presence of infiltration or blockage of flow.

It will be recognized that, in the interest of clarity of illustration, many of the dimensions in the Figures have been exaggerated, particularly radial dimensions such as the diameter of small-bore flow passage 13 and the thicknesses of tubes 20 and 21. Also in the interest of clarity, annuli 23 and 24 are shown in a partially inflated state, whereas in their normal unstressed state they closely fit duct 16 and in their inflated state they bear against the inside of jacket 25.

Attention is now directed to FIG. 3, which is a view, largely in cross-section, of a similar flow restrictor having further means for providing an alarm signal signifying the existence of infiltration. Similar reference numerals refer to similar structures in all the Figures. Attached to jacket 25, preferably by cementing, is a mounting block 28. A threaded hole is provided in block 28 and jacket 25 to accept threaded bushing 29 of membrane switch assembly 30. The sensitive membrane 31 of switch assembly 30 extends just to the inner surface of jacket 25 so that full inflation of annulus 24 will deflect membrane 31 and operate switch contacts (not shown), within membrane switch assembly 30, which may be connected through conductors 32 of cable 33 to external apparatus (not shown) to provide an alarm signal when infusant pressure of at lest 35-110 Torr occurs downstream of small-bore flow passage 13, thus signifying the occurrence of infiltration.

Given the foregoing teaching, those skilled in the art to which this invention pertains may readily devise further or extended embodiments. For one example, upstream annulus 23 may be constructed of a single layer of elastomeric material of suitable thickness and elastic modulus, rather than the two layers shown in the Figures. For another example, instead of using a membrane switch assembly 30 having internal contacts and externally fastened to jacket 25, one could provide conductive coatings, connected to conductors of a cable, on the exterior of annulus 24 and the interior of jacket 25, the coatings thus constituting switch contacts which close when annulus 24 is inflated to touch jacket 25. For yet another example, while the inflatable elastomeric sac elements of the illustrated preferred embodiment have been described and shown as axisymmetric annuli, other forms may be employed, such as bladders of elastomeric material attached to, and inflatable through, duct 16. Various other features and advantages not specifically enumerated will occur to those versed in the art, as likewise many variations of the embodiments which have been illustrated, all of which may be achieved without departing from the spirit and scope of the invention as defined by the following claims:

We claim:

1. A flow restrictor, for use in an infusion system comprising a source of liquid infusate pressurized to a substantially constant known driving pressure driving a flow rate of liquid infusate through sid restrictor, comprising a small-bore flow passage, defined within a length of capillary tubing and having a length and a diameter, the ratio of said length to said diameter being at least 10, and said length being at least 3 millimeters, said flow restrictor being further capable of indicating pressure and flow of said liquid infusate and further comprising: a tubular duct sealably surrounding said capillary tubing and extending upstream and downstream thereof; an upstream hole and a downstream hole in the wall of said duct at locations respectively just upstream and downstream of said capillary tubing; thin-wall elastomeric tubing surrounding said duct and sealed thereto at distances upstream and downstream of said holes to provide sealed upstream and downstream annuli inflatable by pressurized infusate flowing outward through said holes; a transparent cylindrical jacket surrounding said elastomeric tubing and radially spaced therefrom at a small distance such that said elastomeric tubing touches said jacket when said annuli are inflated, the thickness and elastic modulus of said elastomeric tubing providing said downstream annulus being sufficiently small that said downstream annulus may be inflated to touch said jacket when the pressure of said infusate, flowing through said downstream hole, is only 35 to 110 Torr and, the thickness and elastic modulus of said elastomeric tubing providing said upstream annulus being sufficiently large that said upstream annulus may be inflated to touch said jacket only when the pressure of said infusate, flowing through said upstream hole, is at least 200 to 500 Torr.

2. A flow restrictor according to claim 1 in which the inside surface of said transparent cylindrical jacket bears an optically rough surface at locations adjacent said sealed annuli.

3. A flow restrictor according to claim 2 in which the outside surfaces of said sealed annuli are colored.

4. A flow restrictor, for use in an infusion system comprising a source of liquid infusate pressurized to a substantially constant known driving pressure driving a flow rate of liquid infusate through said restrictor, comprising a small-bore flow passage, defined within a length of capillary tubing and having a length and a diameter, the ratio of said length to said diameter being at least 10, and said length being at least 3 millimeters, said flow restrictor being further capable of indicating pressure and flow of said liquid infusate and further comprising: a tubular duct sealably surrounding said capillary tubing and extending upstream and downstream thereof; an upstream hole and a downstream hole in the wall of said duct at locations respectively just upstream and downstream of said capillary tubing; thin-wall elastomeric tubing surrounding said duct and sealed thereto at distances upstream and downstream of said holes to provide sealed upstream and downstream annuli inflatable by pressurized infusate flowing outward through said holes, a transparent cylindrical jacket surrounding said elastomeric tubing and radially spaced therefrom at a small distance such that said elastomeric tubing touches said jacket when annuli are inflated, the thickness and elastic modulus of said elastomeric tubing providing said downstream annulus being sufficiently small that said downstream annulus may be inflated to touch said jacket when the pressure of said infusate, flowing through said downstream hole, is only 35 to 110 Torr, said flow restrictor still further comprising electrical contact means, located outside the downstream annulus of said annuli, adjacent the inflatable portion of said annulus, and mechanically operable by outward motion of said inflatable portion upon full inflation of said annulus.

5. A flow restrictor according to claim 4, in which said electrical contact means is a membrane switch assembly having a sensitive membrane extending inwardly to the inner surface of said transparent cylindrical jacket.

* * * * *